United States Patent [19]

Eckmayer et al.

[11] Patent Number: 5,028,695

[45] Date of Patent: Jul. 2, 1991

[54] PROCESS FOR THE MANUFACTURE OF COLLAGEN MEMBRANES USED FOR HEMOSTASIS, THE DRESSING OF WOUNDS AND FOR IMPLANTS

[75] Inventors: Zdenek Eckmayer, Weinheim, Fed. Rep. of Germany; Ernst Janzen, GR Laren, Netherlands; Günter Rüttgers, Stolberg, Fed. Rep. of Germany

[73] Assignee: Chemokol Gesellschaft Zur Entwicklung von Kollagenprodukten, Fed. Rep. of Germany

[21] Appl. No.: 321,767

[22] Filed: Mar. 10, 1989

[30] Foreign Application Priority Data

Mar. 11, 1988 [EP] European Pat. Off. ........ 88103884.8

[51] Int. Cl.$^5$ ............................................. C07K 15/20
[52] U.S. Cl. .................................... 530/356; 106/161; 8/94.17; 8/74.18; 8/127.5; 435/68.1
[58] Field of Search ....................... 530/356; 435/68.1; 106/161

[56] References Cited

U.S. PATENT DOCUMENTS 4,185,011  1/1980  Eckmayer et al. ................. 530/356
4,404,033  9/1983  Stefffan ............................. 530/356

*Primary Examiner*—Howard E. Schain
*Attorney, Agent, or Firm*—Pravel, Gambrell, Hewitt, Kimbell & Krieger

[57] ABSTRACT

The invention concerns a process for the manufacture of collagen membranes for medical applications, in which process the collagen raw materials obtained from cattle or pig collagen are mechanically freed of fatty residues and treated with diluted alkali and acids and, if need be, enzymes. It is thoroughly washed between these steps to thus clean the collagen raw material eliminating the accompanying contamination. It is then processed further while obtaining a collagen matrix with a dry weight of approximately 25% by weight. Thus obtained are collagen membranes, in which the original integral cohesion remains and with which a fast hemostatic effect is achieved; said membranes are also extremely flexible and they adhere well to the surface of a wound.

12 Claims, No Drawings

PROCESS FOR THE MANUFACTURE OF COLLAGEN MEMBRANES USED FOR HEMOSTASIS, THE DRESSING OF WOUNDS AND FOR IMPLANTS

DESCRIPTION

The invention concerns the manufacture of medical membranes that are suitable for use in the dressing of wounds, for hemostasis or as an implant material.

Collagen has been used for quite some time in medical and particularly in surgical applications. In this respect, the collagen is either in the form of a powder (U.S. Pat. Nos. 3,742,955 and 3,810,473) or in the form of a sponge (U.S. Pat. No. 4,320,201 and U.S. Pat. Des. No. 2,625,289) and may, last but not least, be in the form of fleece (U.S. Pat. Des. No. 2,730,623). The powders, sponges and fleeces from collagen have gained importance in the medical field, because collagen, as a substance from the body, is preferred over substances that are foreign to the body. Collagen sponges exhibit an excellent absorptive capacity, they have a low specific weight and they easily fit the contours of the wound. The adhesion to the wound is often unsatisfactory. Despite the fact that the sponges may be used for the hemostasis of a slow bleeding, they are not suited for the use in a bleeding situation where the blood flows under pressure.

From EP-PS 079 398 a process is known for the manufacture of collagen material for surgical applications, in which Achilles' tendons or skins are processed in an alkaline manner, treated mechanically after a treatment with acid, shrunk, cross linked and dried. From that collagen material, the individual longitudinally oriented fibers are exposed and subsequently processed further in textile machines in a manner commonly used for textiles. In that manner, it is possible to obtain a surgical material with many application possibilities. Since the specific weight of that product is substantially higher than that of a sponge. a faster hemostasis may be achieved with this material than with the sponge. Its mechanical strength in difficult bleeding situations, such as blood flowing under pressure (vascular anastomoses), is, however, not always sufficient; this is particularly true. if an attempt is made to keep injured internal organs in a hemostatic network. Furthermore, the flexibility of the material leaves something to be desired and the fitting to the contours of the wound is thus not always satisfactory.

The presented invention has as its task the making available of medical membranes that are constructed of fine fibers, in which, however, the original integral cohesion remains, that have a fast hemostatic effect, that are flexible and fit very well to the contours of a wound, that have a fast swelling surface which is also flexible and that adheres well to the bleeding surface of a wound. In connection with this task, the membrane should have a high mechanical strength, which makes it possible to use it in that manner as a hemostatic covering, thus ensuring the form, condition and the protection of the injured organ. Great mechanical strength is particularly important, if the membranes are used to cover the bleeding wound and to arrest the bleeding in bleeding situations where the blood flows under pressure.

This task is solved with a collagen membrane that is manufactured with the process in accordance with patent claim 1.

The invention thus concerns a process to manufacture collagen material for medical applications, in which the collagen raw materials from cattle or pig collagen are freed mechanically of fatty residues, treated with diluted alkali and acids and, if need be, with enzymes, thoroughly washed between these steps, thus cleaning the collagen raw material of accompanying contamination, and processed further, while obtaining a collagen matrix with a dry weight of 25% by weight, characterized by the fact that a) the collagen mass is treated with a strong alkali, until the amide nitrogen content is 0.35 mmol/g or less, b) it is subsequently treated with a strong acid at a pH value of 1 or less and then washed with water, thus obtaining a dry weight of between 10 and 14% by weight, in which process the pH value increases to between 2.5 and 3.5.

c) shrinkage is achieved by adding an inorganic saline solution, d) that the material obtained in step c) is squeezed off to a dry weight of between 40 and 50% by weight, e) steps c) and d) are repeated several times, f) the water in the thus obtained matrix is subsequently removed by the adding of a solvent, g) a treatment with further substances (cross-linking agent, softener) is carried out, if need be, and, h) last but not least, the obtained matrix is dried in a stretched form.

Animal collagen such as amnion, chorion, omentum, pericardium and similar are used as the raw material. These products are chemically processed; however, great care is taken to ensure that the original structure of the collagen fiber (the matrix) remains the same. These initial materials are obtained from cattle or pigs.

The producing of collagen materials by the treating of the initial products with alkali, acids, enzymes, salts, cross-linking agents and organic solvents is known.

In that manner collagen fibers are obtained that are more or less denatured. For example, a process for the manufacture of collagen fibers is described in DE-PS 27 30 623, in which the washed and ground initial material is treated at first with alkali and then with acid and subsequently processed mechanically. However, this process produces a collagen material with a low mechanical strength, in which the original collagen matrix and thus the original integral cohesion of the fibers was destroyed. However, it was determined that the properties of the collagen materials are not only a function of the original condition of the fiber, but also a function of the original condition of the structure. For example, the stimulation of the epithelization during the dressing of the wound and the supporting of the stimulation of the granulation tissue are directly connected to the original condition of the structure. It is thus important to note that the presented invention produces a high-grade collagen material, in which the structure of the collagen matrix corresponds to a large degree to the original condition.

The process in accordance with the invention consists of a series of steps that are similar with respect to their technology. In that regard, some of these process steps are basically known from processes used to manufacture collagen materials. However, the exact manner of these process steps and their sequence is important in order to produce the collagen materials in accordance with the presented invention.

The process steps mentioned in the description of patent claim 1 are generally known. This concerns the cleaning of the material. This processing step is, for example, known in the leather industry and in the manufacture of gelatin and is used in a similar manner in the manufacture of sausage skins, in the manufacture of collagen packaging materials and in the manufacture of collagen fibers. This cleaning process consists of the measures indicated below:

The collagen raw material from cattle or pig collagen is initially freed mechanically of fatty residues. The collagen material, thus almost free of fatty residues, is thoroughly washed with water. preferably with running water. This is followed by a treating of the material with alkali such as a diluted approximately 5% NaOH solution. This may again be followed by a washing step, preferably with running water. In the next cleaning step, the material is treated with an acid, preferably hydrochloric acid, in which process the pH value of the acidified material is set to approximately 1 or less. This is again followed by a washing step. A collagen matrix with a dry weight of approximately 25% by weight is obtained in this manner.

The further processing in accordance with the invention consists of, the following steps:

a) The collagen mass that was cleaned in the manner described above is treated with a strong alkali. Sodium hydroxide is the preferred substance used here. The alkaline treating during the manufacture of collagen materials is generally known. This treatment is used to loosen the fibers, which are opened in part and which are also in part modified chemically. This alkaline treatment is continued until the amide nitrogen content is reduced to one half of the initial quantity. This is achieved, when the amide nitrogen content is 0.35 mmol/g collagen or less. This alkaline treatment, which is carried out preferably in a tanner's barrel. lasts between 10 and 15 days.

The treatment with a strong acid takes place in step b). The membranes are initially acidified with an acid, preferably hydrochloric acid. This acid treatment continuous until the material is acidified homogeneously, in general after approximately 1 to 5 hours and preferably after approximately 2 to 3 hours. Relatively strong acids, preferably hydrochloric acids, are used at a concentration of approximately 3%. The material swells only slightly in this treatment, which exhibits a pH value of less than 1.0 after the acid treatment. The material is subsequently washed again with running water. The pH value of the material thus increases to approximately 3.0 (HCl) and the material swells. It now has a dry weight of between 10 and 14% by weight.

The shrinkage of the material occurs in step c). For that purpose, the membranes are treated with a solution of an inorganic salt, preferably common salt. The pH value of this solution is between 2.5 and 3.5 and preferably 3.0. and the concentration of the salt is between 10 and 20% by weight. This treatment lasts for several minutes.

In step d), the material obtained in step c) is squeezed off to a dry weight of between 40 and 50% by weight. In the process in accordance with the invention, this step is very important because of the following fact: the sometimes solid fibrous structure of the membranes is loosened by the strong swelling and shrinking action. However, the shrunk collagen fibers immediately swell again if the salt is washed out of the fibers. It is thus preferred to wash out the salt in accordance with step d).

Steps c) and d) are repeated several times, i.e. at least twice, but preferably three times, in which processes the material changes two or three times between swelled and shrunken states.

In step f), the water in the obtained matrix is removed by adding a solvent. It is important to note that the drying of the shrunk membranes should not occur in air. The individual fibers and fibrils would become completely glued together. Membranes that were dried in that manner are irregularly transparent, have a strongly reduced porosity and the inner surface of the membrane is substantially smaller. This would indicate that the rehydration of the material due to the effect of the hydrophilic liquids would take hours and these materials are thus not suited for the use in surgical applications. In the process in accordance with the invention, the drying step is preferably carried out with acetone. This drying process with acetone results in the complete drawing off of the water and of the acid. The salt that was not washed out previously is not soluble in acetone and thus remains in the membranes.

The thus dried (water removed) matrix is subsequently dried in a stretched form in, for example, air.

If need be, treating with further substances such as cross-linking agents or softeners takes place in step g). This further treatment is of particular interest to modify the collagen materials in accordance with the invention for particular medical fields of application. For example, if the membranes are to be used for implants, a cross-linking would be of interest Such cross-linking processes for collagen materials are generally known. Suitable physiologically safe cross-linking agents are, above all, hexamethylene diisocyanate and polyethylene glycol diglycidol ether. The degree of cross linking may be varied with the amount of the cross-linking agent added. Furthermore, it is also possible to add softeners such as glycerin in steps g). A very flexible polymeric material is obtained in that manner.

Preferred forms of execution are described with the help of the examples indicated below. Example 1 describes a hemostatic membrane that was not subjected to a cross-linking or softening process. Example 2 describes the manufacture of a membrane that is particularly suitable for the dressing of wounds. Finally, example 3 describes a cross-linked membrane that was strengthened by cross-linking with hexamethylene diisocyanate.

EXAMPLE 1: The manufacture of hemostatic membranes

Fat is at first removed to the extent possible from fresh peritoneum membranes obtained from a pig and they are subsequently thoroughly washed with running water. The material is then treated for 24 hours with a 0.5% NaOH solution and again washed with running water. The material is subsequently acidified with HCl and the pH value of the acidified material ia approximately 1.0. The material is then washed with running water until the pH value of the material is between approximately 2.5 and 3.5.

The material is now squeezed off and the fat is removed mechanically in a fleshing machine used by the leather industry. The thus prepared material may now be used for the manufacture of all types of membranes in accordance with the process proposed in the invention.

For the alkaline treatment, the material is treated with 0.3% by weight NaOH for approximately 20 days. The amide nitrogen content in the material is now reduced to a value of 0.36 mmol/g. The treatment takes place in a tanner's barrel and the material is stirred regularly.

The evenly swollen membranes are now washed with running water and subsequently acidified with 3% by weight HCl in the tanner's barrel. The pH value of the material is reduced quickly to below 1.0. The membranes are now completely acidified while being moved. This process lasts for approximately 2 to 3 hours. The material is subsequently washed with running water until the pH value of the membrane reaches 2.9. The dry weight of the membranes is now approximately 11%. The membranes are now placed in a scouring solution consisting of 10% by weight common salt and 100% by weight water; both values are in reference to the weight of the membrane. The material remains in the saline solution for 3 hours and is then squeezed off. The material is subsequently washed with running water until no salt remains. The strongly swelled material is again treated with a common salt solution as described above.

The pH value of the common salt solution is kept at a value of 3.0. These steps are repeated three times, in which processes the material changes three times from the swelled to the shrunken state and is thus loosened. After the last shrinkage step, the membrane is full of holes.

The material is now treated three times with acetone; said process removes the water and dries the material.

To the last acetone scouring solution 5% by weight of water was added (in reference to the membrane weight). The membranes are squeezed off after the acetone treatment. Because of the water that was added, the membranes may now be dried in a stretched condition. After the drying step, the membranes are loose and plane, and the fibers have the largest surface possible. The material is physiologically perfect and may be used for a hemostasis after sterilization.

EXAMPLE 2: Transparent membranes for the dressing of wounds

The raw material is the same as in example 1 and the chemical treatment is the same as described in example 1. The value for the amide nitrogen content was also 0.36 mmol/g and the subsequent treating up to the salt treatment also corresponds to example 1. The membranes are dried three times with acetone. A few drops of hydrochloric acid are added to the last acetone scouring solution. The membranes are subsequently dried in air. The pH value of the aqueous extract of the membrane is 2.8. The membranes are then treated twice with N-hexane. The last residues of the fat that may tarnish the membranes are thus removed. After the hexane treatment, the materials are dried in air and subsequently and thoroughly washed with running water. The pH value of the water is 3.5. The membranes swell now and they are drossed (pushed out) in that state onto a glass plate. This is followed by a drying process in air. During the drying process, the collagen fibers are glued together and this results in a transparent foil that is particularly suited for the dressing of wounds. They allow the observing of the wound after it was covered by the membrane. The membranes are prepared, packaged twice and they may be used immediately after sterilization.

EXAMPLE 3: Cross-linked membranes for implants or the dressing of wounds

The raw material is the same as in example 1 and the chemical treatment is the same as described in example 1. The material is washed twice with acetone after the salt treatment. Potash is added to the acetone already during the first washing step and the same is true for the second washing step. After the washing, the pH value of the water extract is 6.8 (determination: ratio between water : membrane .... 80:20; shaking for 20 minutes; after 20 minutes, centrifuging and measuring of the pH value). The material is now thoroughly washed with running water. This is followed by a drying process with neutral acetone.

The dried membranes are now placed in a scouring solution that consists of 400% by weight acetone and 2% by weight hexamethylene diisocyanate; all numbers are in reference to the weight of the membrane. The membranes are shaken thoroughly for 2 hours. After 2 hours, they are thoroughly washed in running water until the last traces of the HMDIIC smell have disappeared and they are subsequently dried in acetone or after the drossing onto a glass plate. The shrinking temperature of the material is 68° C.

The material is now stamped, packaged twice, and sterilized, and it may be used immediately.

I claim:
1. A process for the manufacture of collagen membranes having an integral cohesion of fine fibers corresponding to that of a collagen raw material, and having a dry weight of approximately 25% by weight consisting essentially of, the step of:
    (a) mechanically freeing fatty residues from a collagen raw material and washing the raw material;
    (b) treating the collagen raw material with a strong alkali unit the amide nitrogen content is less than or equal to 0.35 mmol/g collagen;
    (c) treating the alkali-treated raw material with a strong acid at a pH value of less than or equal to 1 and subsequently washing the treated materials with water to obtain a dry weight of between 10 and 14% by weight, in which process the pH value increases to between 2.5 and 3.5;
    (d) shrinking the washed material by adding thereto an inorganic saline solution;
    (e) swelling the shrunken material by squeezing off the inorganic saline solution and washing the shrunken material with water to reach a dry weight of between 40 and 50% by weight;
    (f) repeating steps (d) and (e) at least twice;
    (g) removing water from the resulting matrix product of step (f) by the addition of a solvent; and
    (h) drying the matrix in a stretched form, to obtain a membrane wherein the integral cohesion of the fibers of the membrane's matrix correspond to that of a collagen raw material and having a dry weight of approximately 25% by weight.
2. A process in accordance with claim 1, characterized by the fact that the alkali treatment in step (b) is carried out with NaOH.
3. A process in accordance with claim 1, characterized by the fact that the acid treatment is carried out with HCl.

4. A process in accordance with claim 1, characterized by the fact that an aqueous common salt solution is used in step (d) as the inorganic saline solution.

5. A process in accordance with claim 1, characterized by the fact that an organic solvent is used in step (g) as the solvent.

6. A process in accordance with claim 5, characterized by the fact that acetone is used as the solvent.

7. A process in accordance with claim 1, wherein prior to drying the material the product of step (g) is treated with a cross-linking agent or softener.

8. A process in accordance with claim 7, characterized by the fact that hexamethylene diisocyanate or polyethylene glycol diglycidol ether are used as the cross-linking agent.

9. A process in accordance with claim 7, characterized by the fact that glycerine is added as the softener.

10. A process in accordance with claim 1, wherein said collagen raw materials obtained from cattle or pig collagen is further treated with an enzyme prior to step (b).

11. The process of claim 1 wherein the collagen raw material is obtained from cattle or pig collagen.

12. The process of claim 1 wherein the collagen raw material is selected from amnion, chorion, omentum, or pericardium membranes.

* * * * *